(12) United States Patent
Brannan

(10) Patent No.: US 8,430,871 B2
(45) Date of Patent: Apr. 30, 2013

(54) SYSTEM AND METHOD FOR MONITORING ABLATION SIZE

(75) Inventor: Joseph D. Brannan, Erie, CO (US)

(73) Assignee: Covidien LP, Mansfield, MA (US)

( * ) Notice: Subject to any disclaimer, the term of this patent is extended or adjusted under 35 U.S.C. 154(b) by 753 days.

(21) Appl. No.: 12/607,221

(22) Filed: Oct. 28, 2009

(65) Prior Publication Data

US 2011/0098696 A1    Apr. 28, 2011

(51) Int. Cl.
    *A61B 18/18* (2006.01)
(52) U.S. Cl.
    USPC .............................. 606/33; 606/41
(58) Field of Classification Search ............... 606/32–45
    See application file for complete search history.

(56) References Cited

U.S. PATENT DOCUMENTS

| | | | |
|---|---|---|---|
| 4,629,847 A | 12/1986 | Gics | |
| 4,643,186 A * | 2/1987 | Rosen et al. | 606/33 |
| 4,945,912 A | 8/1990 | Langberg | |
| 5,246,438 A | 9/1993 | Langberg | |
| 5,369,251 A * | 11/1994 | King et al. | 219/695 |
| 5,370,644 A | 12/1994 | Langberg | |
| 5,549,639 A | 8/1996 | Ross | |
| 5,672,173 A * | 9/1997 | Gough et al. | 606/41 |
| 6,132,425 A * | 10/2000 | Gough | 606/41 |
| 6,222,193 B1 | 4/2001 | Thurston et al. | |
| 6,325,796 B1 | 12/2001 | Berube et al. | |
| 6,380,815 B1 | 4/2002 | Fehrenbach et al. | |
| 6,500,175 B1 * | 12/2002 | Gough et al. | 606/42 |
| 6,575,969 B1 * | 6/2003 | Rittman et al. | 606/41 |
| 6,986,764 B2 | 1/2006 | Davenport et al. | |
| 7,025,765 B2 | 4/2006 | Balbierz et al. | |
| 7,118,590 B1 | 10/2006 | Cronin | |
| 7,300,436 B2 | 11/2007 | Penny et al. | |
| 7,529,398 B2 * | 5/2009 | Zwirn et al. | 382/131 |

(Continued)

FOREIGN PATENT DOCUMENTS

| | | |
|---|---|---|
| DE | 390937 | 3/1924 |
| DE | 1099658 | 2/1961 |
| DE | 1139927 | 11/1962 |
| DE | 1149832 | 6/1963 |

(Continued)

OTHER PUBLICATIONS

European Search Report for European Application No. 10014080 dated Mar. 17, 2011.

(Continued)

*Primary Examiner* — Lee S Cohen
*Assistant Examiner* — Amanda Scott

(57) ABSTRACT

A system for monitoring ablation size is provided and includes a power source including a microprocessor for executing at least one control algorithm. A microwave antenna is configured to deliver microwave energy from the power source to tissue to form an ablation zone. A radiation detection device is operably disposed on the microwave antenna. The radiation detection device is configured to generate a voltage corresponding to a radius of the ablation zone, wherein the radiation detection device is in operative communication with at least one module associated with the power source. The at least one module triggers a signal when a predetermined threshold voltage is measured corresponding to the radius of the ablation zone.

15 Claims, 8 Drawing Sheets

U.S. PATENT DOCUMENTS

| | | | |
|---|---|---|---|
| 2002/0087079 | A1 | 7/2002 | Kaufman et al. |
| 2006/0293651 | A1 | 12/2006 | Cronin |
| 2007/0078453 | A1* | 4/2007 | Johnson et al. ............... 606/32 |
| 2008/0125775 | A1 | 5/2008 | Morris |
| 2008/0319434 | A1* | 12/2008 | Rick et al. .................... 606/33 |
| 2009/0076409 | A1 | 3/2009 | Wu et al. |
| 2010/0036369 | A1* | 2/2010 | Hancock ....................... 606/33 |

FOREIGN PATENT DOCUMENTS

| | | |
|---|---|---|
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 1 159 926 | 5/2001 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | WO 96/39086 | 12/1996 |
| WO | WO 00/49957 | 8/2000 |
| WO | 2004/086995 A1 | 10/2004 |

OTHER PUBLICATIONS

European Search Report EP 10 01 4081 dated Mar. 4, 2011.
U.S. Appl. No. 08/483,742, filed Jun. 7, 1995.
U.S. Appl. No. 08/136,098, filed Oct. 14, 1993.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/251,857, filed Oct. 15, 2008.
U.S. Appl. No. 12/253,457, filed Oct. 17, 2008.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/508,700, filed Jul. 24, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.

U.S. Appl. No. 12/619,462, filed Nov. 16, 2009.
U.S. Appl. No. 12/620,289, filed Nov. 17, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Elecirothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 1n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.

Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite-Element Codes to Model Electrical Heating and Non•Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General, Gynecologic, Urologic, and Laparoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.

European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
European Search Report for EP 10 01 4042 dated Feb. 18, 2011 (6 pages).
European Search Report for European Application No. 11001596.3 dated Jun. 27, 2011.

* cited by examiner

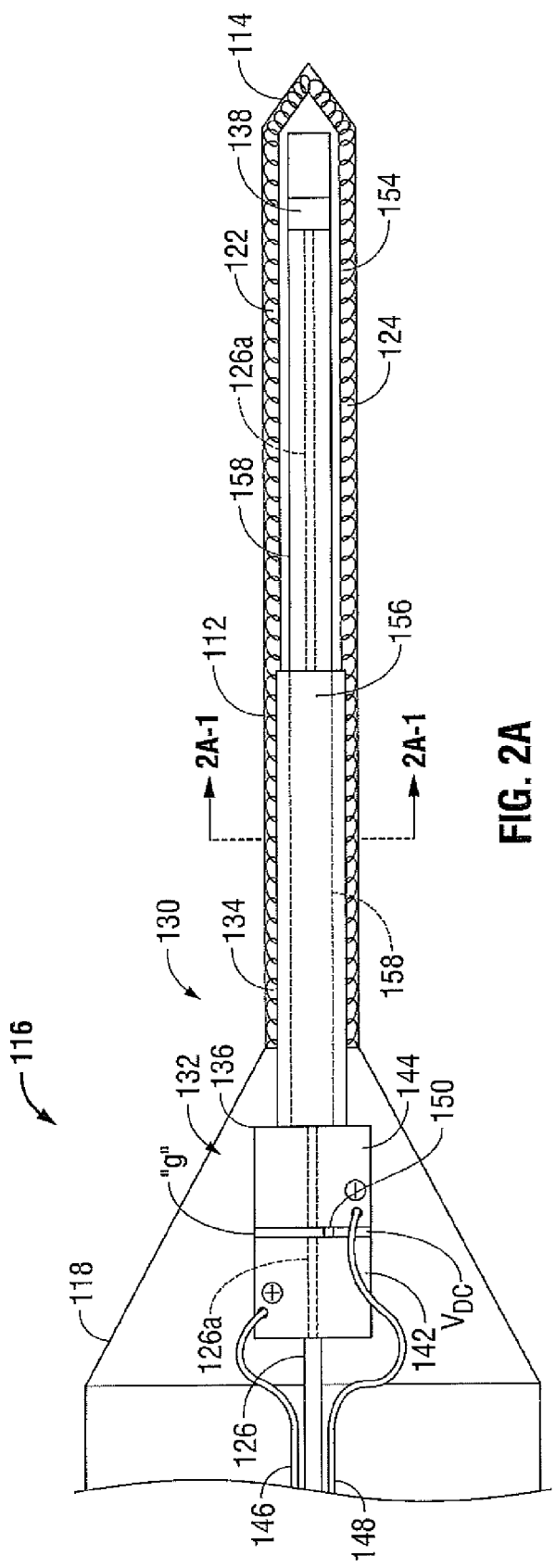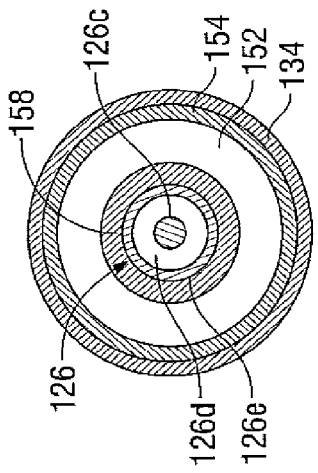

SYSTEM AND METHOD FOR MONITORING ABLATION SIZE

BACKGROUND

1. Technical Field

The present disclosure relates to systems and methods that may be used in tissue ablation procedures. More particularly, the present disclosure relates to systems and methods for monitoring ablation size during tissue ablation procedures in real-time.

2. Background of Related Art

In the treatment of diseases such as cancer, certain types of cancer cells have been found to denature at elevated temperatures (which are slightly lower than temperatures normally injurious to healthy cells). These types of treatments, known generally as hyperthermia therapy, typically utilize electromagnetic radiation to heat diseased cells to temperatures above 41° C. while maintaining adjacent healthy cells at lower temperatures where irreversible cell destruction will not occur. Procedures utilizing electromagnetic radiation to heat tissue may include ablation of the tissue.

Microwave ablation procedures, e.g., such as those performed for menorrhagia, are typically done to ablate the targeted tissue to denature or kill the tissue. Many procedures and types of devices utilizing electromagnetic radiation therapy are known in the art. Such microwave therapy is typically used in the treatment of tissue and organs such as the prostate, heart, and liver.

One non-invasive procedure generally involves the treatment of tissue (e.g., a tumor) underlying the skin via the use of microwave energy. The microwave energy is able to non-invasively penetrate the skin to reach the underlying tissue. However, this non-invasive procedure may result in the unwanted heating of healthy tissue. Thus, the non-invasive use of microwave energy requires a great deal of control.

Currently, there are several types of systems and methods for monitoring ablation zone size. In certain instances, one or more types of sensors (or other suitable devices) are operably associated with the microwave ablation device. For example, in a microwave ablation device that includes a monopole antenna configuration, an elongated microwave conductor may be in operative communication with a sensor exposed at an end of the microwave conductor. This type of sensor is sometimes surrounded by a dielectric sleeve.

Typically, the foregoing types of sensor(s) are configured to function (e.g., provide feedback to a controller for controlling the power output of a power source) when the microwave ablation device is inactive, i.e., not radiating. That is, the foregoing sensors do not function in real-time. Typically, the power source is powered off (or pulsed off) when the sensors are providing feedback (e.g., tissue temperature) to the controller and/or other device(s) configured to control the power source.

SUMMARY

The present disclosure provides a system for monitoring ablation size in real-time. The system includes a power source including a microprocessor for executing at least one control algorithm. The system includes a microwave antenna configured to deliver microwave energy from the power source to tissue forming an ablation zone. A radiation detection device is operably disposed on the microwave antenna. The radiation detection device configured to generate a voltage corresponding to a radius of the ablation zone. The radiation detection device is in operative communication with at least one module associated with the power source, wherein the at least one module triggers a signal when a predetermined threshold voltage is measured corresponding to the radius of the ablation zone.

The present disclosure provides a microwave antenna adapted to connect to a power source configured for performing an ablation procedure. The microwave antenna includes a radiating section configured to deliver microwave energy from the power source to tissue to form an ablation zone. A radiation detection device is operably disposed on the microwave antenna. The radiation detection device configured to generate a voltage corresponding to a radius of the ablation zone. The radiation detection device is in operative communication with one or more modules associated with the power source, wherein the at least one module triggers a signal when a predetermined threshold voltage is measured corresponding to the radius of the ablation zone.

In one particular embodiment, the one or more modules include an ablation zone control module is in operative communication with a memory associated with the power source. The memory includes one or more data look-up tables including rectified dc voltages associated with the microwave antenna. The rectified dc voltages correspond to a radius of the ablation zone. The ablation control module is configured to instruct the power source to adjust the amount of microwave energy being delivered to the microwave antenna when a signal from radiation detection device is received at the ablation zone control module to create a uniform ablation zone of suitable proportion with minimal damage to adjacent tissue.

In an embodiment, a portion of the radiation detection device is operably positioned at a distal end of a handle associated with the microwave antenna and extends within an internal portion of a shaft associated with the microwave antenna.

In an embodiment, the ablation zone control module and radiation detection device are activated when the power source is activated. Alternatively, the ablation zone control module and radiation detection device are activated when the power source is deactivated. In an embodiment, the radiation detection device includes a resonator in electrical communication with a resonator coaxial feed extending distally along a length of the shaft. A distal end of the resonator coaxial feed is positioned adjacent a radiating section of the microwave antenna and is configured to detect radiation during the delivery of microwave energy from the power source to tissue and induce an electromagnetic field within the resonator such that a rectified dc voltage is generated at the resonator and communicated to the ablation zone control module. The resonator coaxial feed may be made from a metal selected from the group consisting of copper, silver and gold. In one particular embodiment, the resonator is a substantially enclosed structure for resonating an electromagnetic field within the resonator. The resonator may be generally cylindrical and made from a metal selected from the group consisting of copper, silver and gold.

In an embodiment, the resonator includes a generally circumferential gap dividing the resonator into two conductive portions in electrical communication with one another and electrically isolated from one another. The two conductive portions are in electrical communication with the ablation zone control module via a pair of conductive leads. One or more diodes extend across the gap and operably couples to each of the two conductive portions of the resonator. The one or more diodes is configured to produce a rectified dc voltage that corresponds to the electromagnetic field within the resonator.

In an embodiment, a dielectric coating may be disposed between the shaft and the resonator coaxial feed to prevent electrical shorting between the resonator coaxial feed and the shaft.

In an embodiment, the microwave antenna may be configured to produce an ablation zone that is spherical.

In an embodiment, the microwave antenna may be configured to produce an ablation zone that is ellipsoidal.

The present disclosure also provides a method for monitoring temperature of tissue undergoing ablation. The method includes an initial step of transmitting microwave energy from a power source to a microwave antenna to form a tissue ablation zone. A step of the method includes monitoring complex impedance associated with the microwave antenna as the tissue ablation zone forms. A step of the method includes communicating a control signal to the power source when a predetermined rectified dc voltage is reached at the microwave antenna. Adjusting the amount of microwave energy from the power source to the microwave antenna is another step of the method.

BRIEF DESCRIPTION OF THE DRAWINGS

The above and other aspects, features, and advantages of the present disclosure will become more apparent in light of the following detailed description when taken in conjunction with the accompanying drawings in which:

FIG. 2A is partial cut-away view of a distal tip of a microwave antenna depicted in FIG. 1A;

FIG. 2A-1 is a cross-section view taken along line segment 2A-1 of FIG. 2A;

DETAILED DESCRIPTION

Figure 1A:
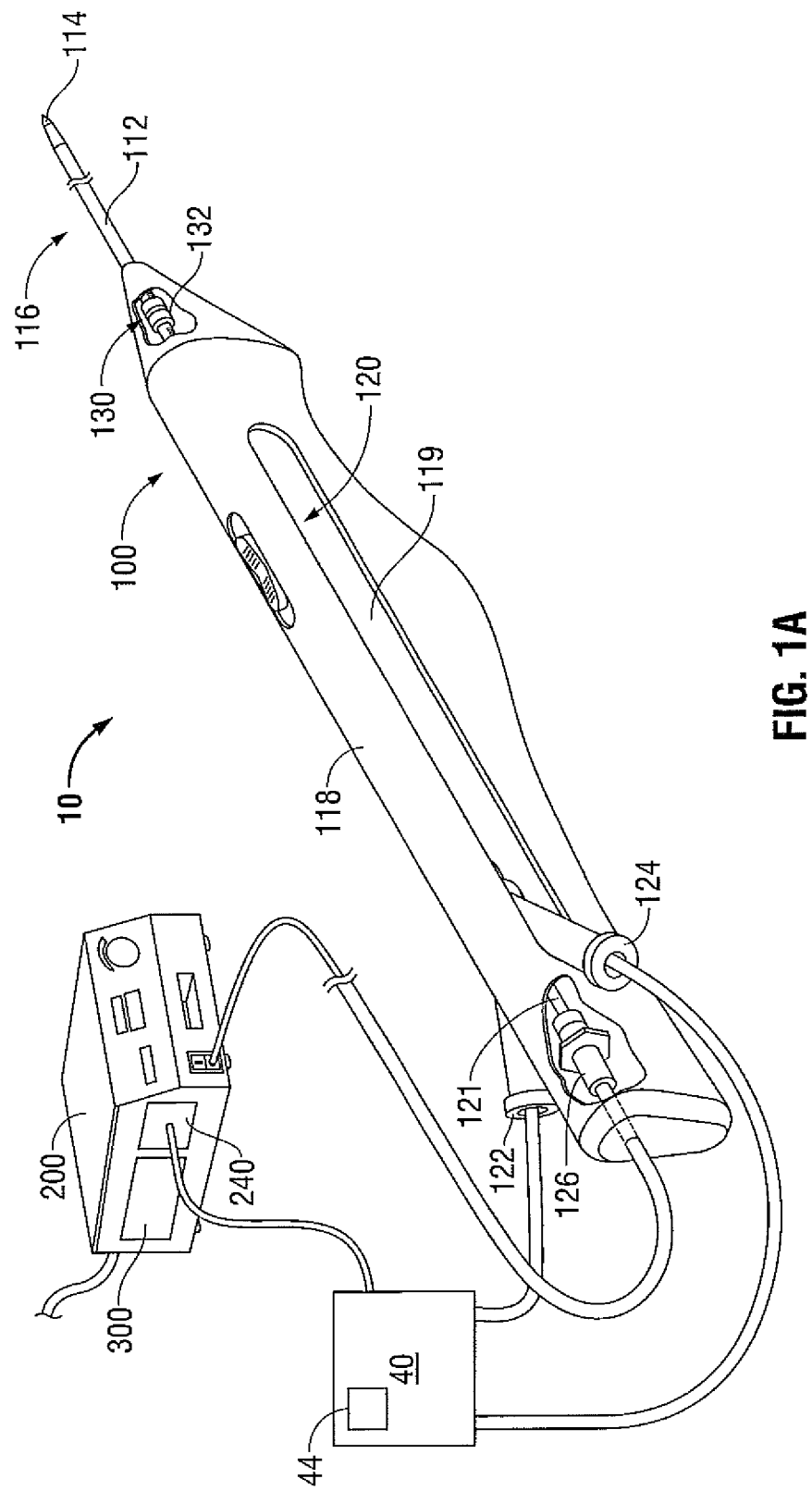
FIG. 1A is a perspective view of a system for monitoring ablation size according to an embodiment of the present disclosure.
Figure 1B:
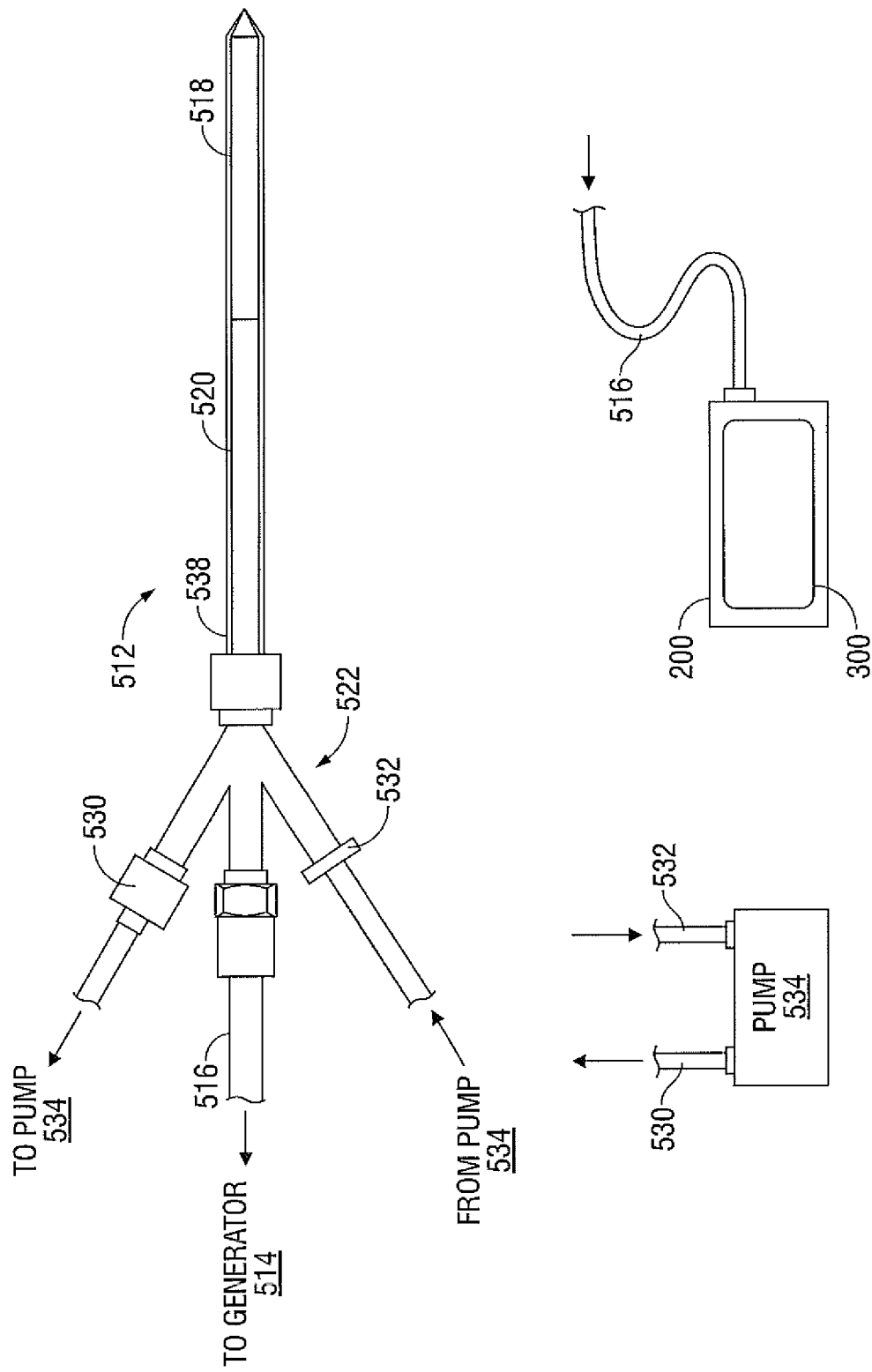
FIG. 1B is a perspective view of a system for monitoring ablation size according to another embodiment of the present disclosure.

Embodiments of the presently disclosed system and method are described in detail with reference to the drawing figures wherein like reference numerals identify similar or identical elements. As used herein and as is traditional, the term "distal" refers to a portion that is furthest from the user and the term "proximal" refers to a portion of the microwave antenna that is closest to the user. In addition, terms such as "above," "below," "forward," "rearward," etc. refer to the orientation of the figures or the direction of components and are simply used for convenience of description.

Referring now to FIG. 1A, a system for monitoring ablation size in accordance with an embodiment of the present disclosure is designated 10. The system 10 includes a microwave antenna 100 that is adapted to connect to an electrosurgical power source, e.g., an RF and/or microwave (MW) generator 200 that includes or is in operative communication with one or more controllers 300 and, in some instances, a fluid supply pump 40. Briefly, microwave antenna 100 includes an introducer 116 having an elongated shaft 112 and a radiating or conductive section or tip 114 operably disposed within elongated shaft 112, a cooling assembly 120 having a cooling sheath 121, a handle 118, a cooling fluid supply 122 and a cooling fluid return 124, and an electrosurgical energy connector 126. Connector 126 is configured to connect the microwave antenna 100 to the electrosurgical power source 200, e.g., a generator or source of radio frequency energy and/or microwave energy, and supplies electrosurgical energy to the distal portion of the microwave antenna 100. Conductive tip 114 and elongated shaft 112 are in electrical communication with connector 126 via an internal coaxial cable 126a that extends from the proximal end of the microwave antenna 100 and includes an inner conductor tip that is operatively coupled to a radiating section 138 operably disposed within the shaft 112 and adjacent the conductive or radiating tip 114 (see FIG. 2A, for example). As is common in the art, internal coaxial cable 126a is includes a dielectric material and an outer conductor surrounding each of the inner conductor tip and dielectric material. A connection hub (not shown) disposed at a proximal end of the microwave antenna 100 operably couples connector 126 to internal coaxial cable 126a, and cooling fluid supply 122 and a cooling fluid return 124 to a cooling assembly 120. Radiating section 138 by way of conductive tip 114 (or in certain instances without conductive tip 114) is configured to deliver radio frequency energy (in either a bipolar or monopolar mode) or microwave energy to a target tissue site. Elongated shaft 112 and conductive tip 114 may be formed of suitable conductive material including, but not limited to copper, gold, silver or other conductive metals having similar conductivity values. Alternatively, elongated shaft 112 and/or conductive tip 114 may be constructed from stainless steel or may be plated with other materials, e.g., other conductive materials, such as gold or silver, to improve certain properties, e.g., to improve conductivity, decrease energy loss, etc. In an embodiment, the conductive tip may be deployable from the elongated shaft 112.

In an alternate embodiment, system 10 may be configured for use with a microwave antenna 512 illustrated in FIG. 1A. Briefly, microwave antenna 512 is coupled to a generator 200 including a controller 300 via a flexible coaxial cable 516. In this instance, generator 200 is configured to provide microwave energy at an operational frequency from about 500 MHz to about 10 GHz. Microwave antenna 512 includes a radiating portion 518 that may be connected by feedline 20 (or shaft) to the cable 516. More specifically, the microwave antenna 512 is coupled to the cable 516 through a connection hub 522. The connection hub 522 also includes an outlet fluid port 530 (similar to that of cooling fluid return 124) and an inlet fluid port 532 (similar to that of cooling fluid supply 122) that are connected in fluid communication with a sheath 538. The sheath 538 encloses the radiating portion 518 and the feedline 520 allowing for coolant fluid from the ports 530 and 532 to be supplied and circulated around the antenna assembly 512. The ports 530 and 532 are also coupled to a supply pump 534 (similar to that of fluid supply pump 40). For a more detailed description of the microwave antenna 512 and operative components associated therewith, reference is made to commonly-owned U.S. patent application Ser. No. 12/401,268 filed on Mar. 10, 2009.

For the remainder of the disclosure the operative components associated with the system 10 are described with reference to microwave antenna 100.

With reference to FIG. 2A, a radiation detection device 130 is in operative communication with the microwave antenna 100, controller 300, and/or generator 200. Radiation detection device 130 is configured to generate a rectified dc voltage Vdc that corresponds to a radius "r" of an ablation zone "A" associated with an ablation procedure. To this end, radiation detection device 130 is in operative communication with one or more modules (e.g., an ablation zone control module "AZCM 332") associated with the generator 200. In one particular embodiment, the AZCM 332 triggers a signal when a predetermined rectified dc voltage, e.g., Vdc5, is measured corresponding to the radius "r" of the ablation zone "A" (described in greater detail below).

With continued reference to FIG. 2A, the components of radiation detection device 130 are now described. Radiation detection device 130 includes a resonator portion 132 in electrical communication with a resonator coaxial feed 134. In the embodiment illustrated in FIGS. 1A and 2A, resonator 132 is operably disposed within an internal portion of the handle 118 adjacent the elongated shaft 112. The relatively large volume of the handle 118 (when compared to other components, e.g., shaft 112, associated with the microwave antenna 100) provides a larger volume for the resonator 132 to be designed within. Moreover, a hub (e.g., a hub similar to hub 522 associated with microwave antenna 512) associated with the fluid cooled supply and return lines 122 and 124, respectively, provides a useful dielectric loading (e.g., saline, water, etc.) that can be utilized to reduce the size of the resonator 132 for a given frequency of operation.

In accordance with the present disclosure, an electromagnetic field is induced within the resonator 132 and resonates within the resonator 132 during an ablation procedure. To this end, resonator 132 is a substantially enclosed structure having dimensions of suitable proportion. More particularly, a generally circumferential gap "g" essentially divides or separates the resonator 132 into two spaced-apart conductive portions 142 and 144 that are in electrical communication with one another and electrically insulated from one another (i.e., to prevent shorting between the conductive portions 142 and 144). Gap "g" provides a location of high voltage potential, e.g., Vdc, between the two conductive portions 142 and 144. Gap "g" may have any suitable dimensions. In certain embodiments, the gap "g" may partially divide or separate the resonator 132. While the embodiment illustrated in FIGS. 1A and 2A illustrates conductive portions 142 and 144 collectively defining the resonator 132 with a generally cylindrical configuration, it is within the purview of the present disclosure that resonator 132 may have any suitable configuration, e.g., rectangular, square, etc. One or both of the conductive portions 142 and 144 operably couples to the radiating section 138. More particularly, a distal end 136 of the conductive portion 144 operably couples to the resonator coaxial feed 134 that extends distally toward the radiating section 138 along a length of an internal electrical feed tube 158 that houses the internal cable 126a (see FIG. 2A, for example). In the embodiment illustrated in FIG. 2A, internal electrical feed tube 158 supports the conductive members 142 and 144 and/or resonator coaxial feed 134 in a substantially fixed position. Alternatively, one or more components (e.g., an internal wall or other suitable structure) associated with the microwave antenna 100 may operably couple to the radiation detection device 130, or components associated therewith, e.g., one or both of the conductive portions 142 and 144. For example, one or both of the conductive portions 142 and 144 of radiation detection device 130 may be secured to an internal frame associated with the microwave antenna 100. Resonator 132 including conductive portions 142 and 144 may be made from any suitable material. In the embodiment illustrated in FIG. 2A, resonator 132 including conductive portions 142 and 144 is made from one or more types of metal having conductive properties conducive for inducing an electromagnetic field within the resonator 132, such that the electromagnetic field resonates therein for a time sufficient to provide a voltage drop at or across the gap "g." More particularly, resonator 132 including conductive portions 142 and 144 is made from a metal selected from the group consisting of copper, silver, gold, stainless steal, chrome and brass. In one particular embodiment, the conductive portions 142 and 144 are each made from copper.

One or more conductive leads operably couple to one or more components associated with the resonator 132 to provide electrical communication between one or more modules, e.g., AZCM 332, of the controller 300 and/or generator 200. More particularly, conductive portions 142 and 144 are in electrical communication with the AZCM 332 via a respective conductive lead 146 and 148. In the embodiment illustrated in FIG. 2A, conductive lead 146 connects to a positive terminal associated with one or more modules, e.g., AZCM 332, of the generator 300 and/or controller 200. Similarly, conductive lead 148 connects to a negative terminal associated with one or more modules, e.g., AZCM 332, of the generator 300 and/or controller 200. Leads 146 and 148 may secure to the respective conductive portions 142 and 144 via any suitable securement methods known in the relevant art, e.g., solder, electrical contacts or clips, and so forth. The leads 146 and 148 may follow the same electrical line feed paths as internal cable 126a, as best seen in FIG. 2A.

One or more diodes 150 (one diode 150 is shown in the representative drawings) extend across the gap "g" and operably couple to each of the two conductive portions 142 and 144 of the resonator 132 such that a voltage drop across the diode 150 may be achieved when an electromagnetic field is induced within the resonator 132. Diode 150 is configured to produce a rectified dc voltage Vdc that corresponds to the resonating electromagnetic field within the resonator 130 at a time "t" (see FIG. 3B, for example). In an embodiment, a plurality of diodes 150 (not explicitly shown) may operably couple to the conductive portions 142 and 144 and may be configured to function as a full or half wave rectifier. Diode 150 may provide additional structural support to the two conductive members 142 and 144. That is, the diode 150 may facilitate in maintaining the conductive portions 142 and 144 in a substantially fixed and spaced-apart relation with respect to one another. Alternatively, or in combination therewith, one or more non-conductive members, e.g., non-conductive bridges (not shown), may be provided at predetermined locations between the two conductive portions 142 and 144 and along the gap "g." More particularly, the non-conductive bridges extend from one conductive portion, e.g., conductive portion 142, to the other conductive portion, e.g., conductive portion 144, to maintain the conductive portions 142 and 144 in a substantially fixed and spaced apart relation with respect to one another. The non-conductive bridges may be made from any suitable material, such as, for example, thermal plastics with high melting points.

Resonator coaxial feed 134 is in electrical communication with the resonator 132. More particularly, resonator coaxial feed 134 is in electrical communication with one or both conductive portions 142 and 144. In the embodiment illustrated in FIG. 2A, resonator coaxial feed 134 is in electrical communication with conductive portion 144 (as best seen FIG. 2A). As noted above, resonator coaxial feed 134 extends distally from distal end 136 of the conductive member 144 along internal electrical feed tube 158 toward the radiating section 138. A distal end 156 of the resonator coaxial feed 134 is positioned in the general proximity of radiating section 138 of the microwave antenna 100 and configured to detect radiation during the delivery of microwave energy from the generator 200 to tissue such that an electromagnetic field is induced within the resonator 132. Resonator coaxial feed 134 may be made from any suitable material (e.g., metal) that is capable of detecting radiation and inducing an electromagnetic field within the resonator 132. In one particular embodiment, resonator coaxial feed 134 is made from copper. In an alternate embodiment, resonator coaxial feed 134 may be made from a combination of metals such as, for example, the combination of metals selected from the group consisting of copper, gold and silver. A dielectric coating 152 is operably disposed between the internal electrical feed tube 158 and the resonator coaxial feed 134 to prevent electrical shorting between the resonator coaxial feed 134 and the internal electrical feed tube 158, or operative components associated therewith, e.g., internal cable 126a and/or radiating section 138. In one particular embodiment, the combination of a catheter 154 associated with the microwave antenna 100 and one or both of the cooling fluid lines, e.g., cooling fluid supply line 122 and cooling fluid return lines 124, may also serve as a dielectric coating 152. In certain embodiments, a dielectric coating 152 may be operably disposed between the shaft 112 and the resonator coaxial feed 134 to prevent electrical shorting between the resonator coaxial feed 134 and the shaft 112 or operative components associated therewith, e.g., conductive tip 114.

Figure 4:
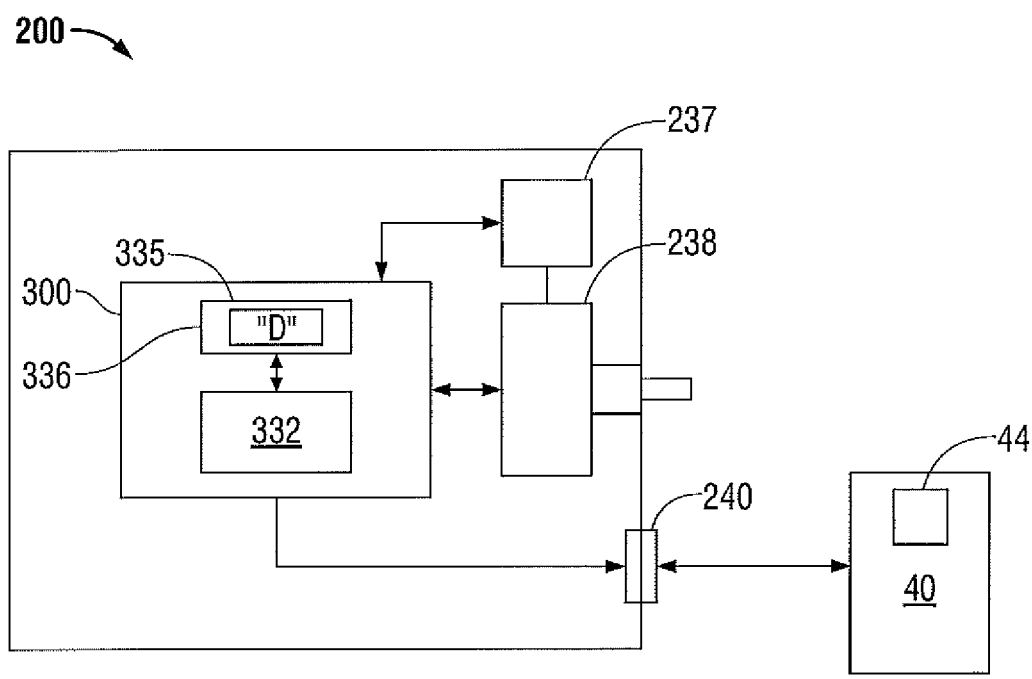
FIG. 4 is a functional block diagram of a power source for use with the system depicted in FIG. 1A.

With reference to FIG. 4, a schematic block diagram of the generator 200 is illustrated. The generator 200 includes a controller 300 having one or more modules (e.g., an ablation zone control module 332 (AZCM 332), a power supply 237 and a microwave output stage 238). In this instance, generator 200 is described with respect to the delivery of microwave energy. The power supply 237 provides DC power to the microwave output stage 238 which then converts the DC power into microwave energy and delivers the microwave energy to the radiating section 138 of the microwave antenna 100. The controller 300 may include analog and/or logic circuitry for processing sensed values provided by the AZCM 332 and determining the control signals that are sent to the generator 200 and/or supply pump 40 via a microprocessor 335. The controller 300 (or component operably associated therewith) accepts one or more measured signals indicative of a rectified dc voltage (e.g., dc voltage Vdc generated by the resonator 132 of the radiation detection device) associated with the microwave antenna 100 when the microwave antenna 100 is radiating energy.

One or more modules e.g., AZCM 332, of the controller 300 analyzes the measured signals and determines if a threshold rectified dc voltage(s) Vdc, e.g., Vdc5, corresponding to an ablation zone "A" having a corresponding radius "r", e.g., radius r5, has been met. If the threshold rectified dc voltage(s) (e.g., Vdc5) has been met, then the AZCM 332, microprocessor 335 and/or the controller instructs the generator 200 to adjust the microwave output stage 238 and/or the power supply 237 accordingly. Additionally, the controller 300 may also signal the supply pump to adjust the amount of cooling fluid to the microwave antenna 100 and/or the surrounding tissue. The controller 200 includes microprocessor 335 having memory 336 which may be volatile type memory (e.g., RAM) and/or non-volatile type memory (e.g., flash media, disk media, etc.). In the illustrated embodiment, the microprocessor 335 is in operative communication with the power supply 237 and/or microwave output stage 238 allowing the microprocessor 335 to control the output of the generator 300 according to either open and/or closed control loop schemes. The microprocessor 335 is capable of executing software instructions for processing data received by the AZCM 332, and for outputting control signals to the generator 300 and/or supply pump 40, accordingly. The software instructions, which are executable by the controller 300, are stored in the memory 336.

Figure 3A:
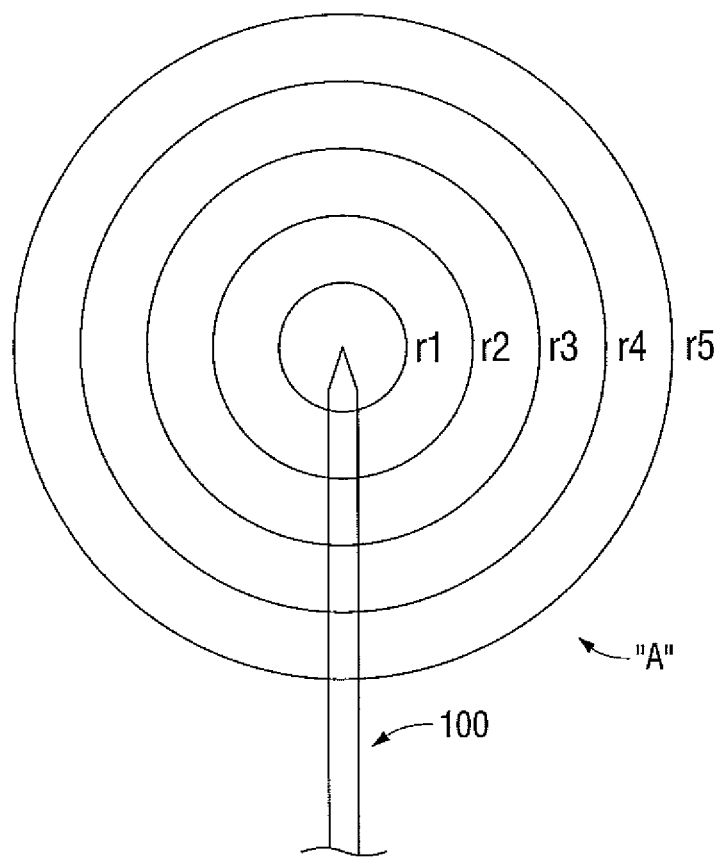
FIG. 3A is a schematic, plan view of the tip of a microwave antenna depicted in FIG. 2A illustrating radial ablation zones associated with the microwave antenna during activation and having a spherical configuration.
Figure 3B:
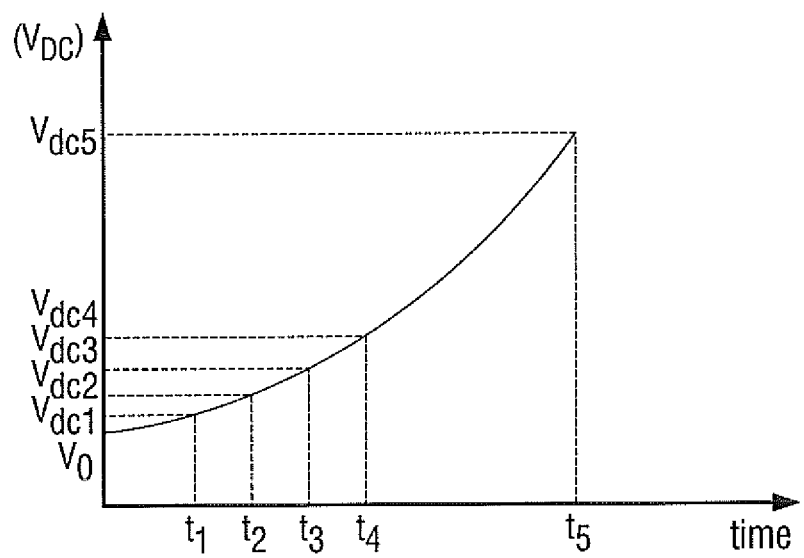
FIG. 3B is a graphical representation of a rectified dc voltage (Vdc) versus time (t) curve.

One or more control algorithms for predicting tissue ablation size is implemented by the controller 300. More particularly, the concept of correlating a rectified dc voltage (e.g., a rectified dc voltage Vdc generated by the resonator 132) associated with a particular microwave antenna, e.g., the microwave antenna 100, with an ablation zone "A" having a radius "r" may be used to indicate tissue death or necrosis. A relationship of the generated rectified dc voltage Vdc as a function of time "t" is illustrated in FIG. 3B. As a microwave ablation cycle progresses, electromagnetic radiation at a "near field," e.g., area adjacent the ablation site, of the microwave antenna 100 varies (e.g., increases) over the course of the ablation cycle due to tissue complex permittivity change caused by temperature increase. When the microwave antenna 100 has heated tissue to a desired temperature, a desired ablation zone "A" having a corresponding radius "r" is (e.g., radius r1,) is formed and electromagnetic radiation is emitted at the "near field." Resonant coaxial feed 134 of the radiation detection device 130 detects the electromagnetic radiation and induces an electromagnetic field within the resonator 132 such that a corresponding dc voltage, e.g., Vdc1, is generated and communicated to the ACZM 332. More particularly, diode 150 produces rectified dc voltages Vdc1-Vdc5 that corresponds to the resonating electromagnetic field within the resonator 130 at times t1-t5, see FIG. 3B, for example).

It should be noted, that the amount of electromagnetic radiation emitted at the "near field" may vary for a given microwave antenna. Factors that may contribute to a specific amount of electromagnetic radiation for a given microwave antenna include but are not limited to: dimensions associated with the microwave antenna (e.g., length, width, etc.); type of material used to manufacture the microwave antenna (or portion associated therewith, e.g., a radiating section) such as copper, silver, etc; and the configuration of a conductive tip associated with the microwave antenna (e.g., sharp, blunt, curved, etc).

Figure 3C:
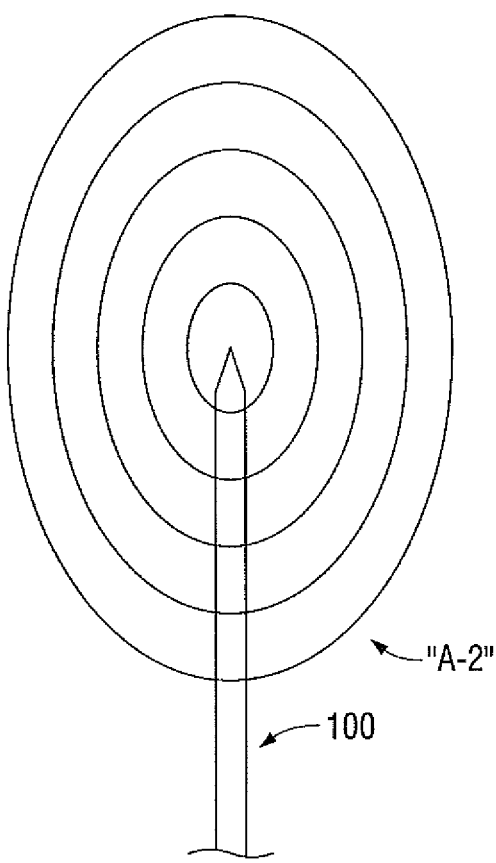
FIG. 3C is a schematic, plan view of the tip of a microwave antenna depicted in FIG. 2A illustrating radial ablation zones associated with the microwave antenna during activation and having an ellipsoidal configuration.

The microwave antenna 100 of the present disclosure may be configured to create an ablation zone "A" having any suitable configuration, such as, for example, spherical (FIG. 3A), hemispherical, ellipsoidal (FIG. 3C where the ablation zone is designated "A-2"), and so forth. In one particular embodiment, microwave antenna 100 is configured to create an ablation zone "A" that is spherical (see FIG. 3A, for example). As noted above, when the microwave antenna 100 has heated tissue in the "near field" to a specific temperature, e.g., at time t1, electromagnetic radiation is emitted at the "near field" and detected by resonant coaxial feed 134 such that an electromagnetic radiation is induced within the resonator 132, which, turn generates a corresponding rectified dc voltage, e.g., Vdc1, that is communicated to the ACZM 332. Correlating the rectified dc voltage Vdc associated with the microwave antenna 100 with the ablated tissue, indicates a specific size (e.g., radius r1) and shape (e.g., spherical) of the ablation zone "A." Thus, a measure of the rectified dc voltage Vdc, e.g., Vdc1 associated with the microwave antenna 100 corresponds to an ablation zone "A" having a radius "r", e.g., radius r1. The control algorithm of the present disclosure uses known rectified dc voltages, Vdc1-Vdc5 associated with specific microwave antennas at specific radii to predict an ablation size. That is, threshold voltages, e.g., Vdc5, associated with a specific microwave antenna, e.g., microwave antenna 100, and corresponding radius, e.g., r5, are compiled into one or more look-up tables "D" and are stored in memory, e.g., memory 336, accessible by the microprocessor 335 and/or the AZCM 332. Thus, when the threshold rectified dc voltage Vdc for a specific microwave antenna, e.g., microwave antenna 100, reaches, for example, Vdc5 one or more modules, e.g. AZCM 332, associated with the controller 300, commands the controller 200 to adjust the power output to the microwave antenna 100 accordingly. This combination of events will provide an ablation zone "A" with a radius approximately equal to r5.

In the illustrated embodiments, for a given microwave antenna, e.g., microwave antenna 100, voltage measurements are taken at times t1-t5. In this instance, voltages, e.g., Vdc1-Vdc5, associated with the microwave antenna 100 may be correlated with an ablation zone "A" defined by a plurality of concentric ablation zones having radii r1-r5 (collectively referred to as radii r) when measured from the center of the ablation zone "A." In this instance, when specific dc voltages, e.g., Vdc3, is met one or more modules, e.g. AZCM 332, associated with the controller 300, commands the controller 200 to adjust the power output to the microwave antenna 100 accordingly.

AZCM 332 may be a separate module from the microprocessor 335, or AZCM 332 may be included with the microprocessor 335. In an embodiment, the AZCM 332 may be operably disposed on the microwave antenna 100. The AZCM 332 may include control circuitry that receives information from one or more control modules, and provides the information to the controller 300 and/or microprocessor 335. In this instance, the AZCM 332, microprocessor 335 and/or controller 300 may access look-up table "D" and confirm that a threshold rectified dc voltage Vdc (e.g., Vdc5) associated with microwave assembly 100 that corresponds to a specific ablation zone, e.g., specific ablation zone having a radius $r_5$, has been met and, subsequently instruct the generator 200 to adjust the amount of microwave energy being delivered to the microwave antenna. In one particular embodiment, look-up table "D" may be stored in a memory storage device (not shown) associated with the microwave antenna 100. More particularly, a look-up table "D" may be stored in a memory storage device operatively associated with handle 118 and/or connector 126 of the microwave antenna 100 and may be downloaded, read and stored into microprocessor 335 and/or memory 336 and, subsequently, accessed and utilized in a manner described above; this would do away with reprogramming the generator 200 and/or controller 300 for a specific microwave antenna. The memory storage device may also be configured to include information pertaining to the microwave antenna 100. For example, information such as, the type of microwave antenna, the type of tissue that the microwave antenna is configured to treat, the type of ablation zone, etc. may be stored into the storage device associated with the microwave antenna. In this instance, for example, generator 200 and/or controller 300 of system 10 may be adapted for use with a microwave antenna configured to create an ablation zone, e.g. ablation zone "A-2," different from that of microwave antenna 100 that is configured to create an ablation zone "A."

In the embodiment illustrated in FIG. 1A, the generator 200 is shown operably coupled to fluid supply pump 40. The fluid supply pump 40 is, in turn, operably coupled to the supply tank 44. In embodiments, the microprocessor 335 is in operative communication with the supply pump 40 via one or more suitable types of interfaces, e.g., a port 240 operatively disposed on the generator 200, that allows the microprocessor 335 to control the output of a cooling fluid 42 from the supply pump 40 to the microwave antenna 100 according to either open and/or closed control loop schemes. The controller 300 may signal the supply pump 40 to control the output of cooling fluid 42 from the supply tank 44 to the microwave antenna 100. In this way, cooling fluid 42 is automatically circulated to the microwave antenna 100 and back to the supply pump 40. In certain embodiments, a clinician may manually control the supply pump 40 to cause cooling fluid 42 to be expelled from the microwave antenna 100 into and/or proximate the surrounding tissue.

Operation of system 10 is now described. Initially, microwave antenna 100 is connected to generator 200. In one particular embodiment, one or more modules, e.g., AZCM 332, associated with the generator 200 and/or controller 300 reads and/or downloads data from a storage device associated with the microwave antenna 100, e.g., the type of microwave antenna, the type of tissue that is to be treated, etc. Thereafter, generator 200 may be activated supplying microwave energy to radiating section 138 of the microwave antenna 100 such that the tissue may be ablated. During tissue ablation, when a predetermined rectified dc voltage Vdc, e.g., V5, at the resonator 132 of the microwave antenna 100 is reached (i.e., a rectified voltage across diode 150 is present), the AZCM 332 instructs the generator 200 to adjust the microwave energy accordingly. In the foregoing sequence of events the AZCM 332 functions in real-time controlling the amount of microwave energy to the ablation zone such that a uniform ablation zone of suitable proportion (e.g., ablation zone "A" having a radius r5) is formed with minimal or no damage to adjacent tissue.

Figure 5:
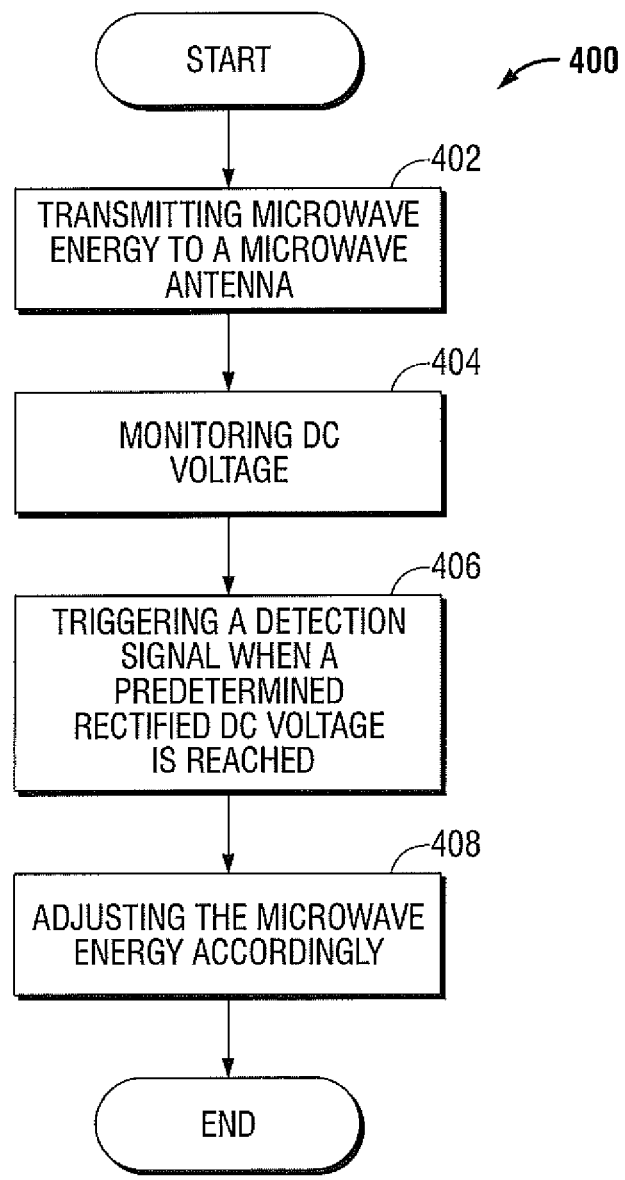
FIG. 5 is a flow chart illustrating a method for monitoring temperature of tissue undergoing ablation in accordance with the present disclosure.

With reference to FIG. 5 a method 400 for monitoring temperature of tissue undergoing ablation is illustrated. At step 402, microwave energy from generator 200 is transmitted to a microwave antenna 100 adjacent a tissue ablation site. At step, 404, dc voltage Vdc associated with the microwave antenna 100 is monitored. At step 406, a detection signal is communicated to the generator 200 when a predetermined rectified dc voltage Vdc is reached at the microwave antenna 100. At step 408, the amount of microwave energy from the generator 200 to the microwave antenna 100 may be adjusted.

Figure 6:
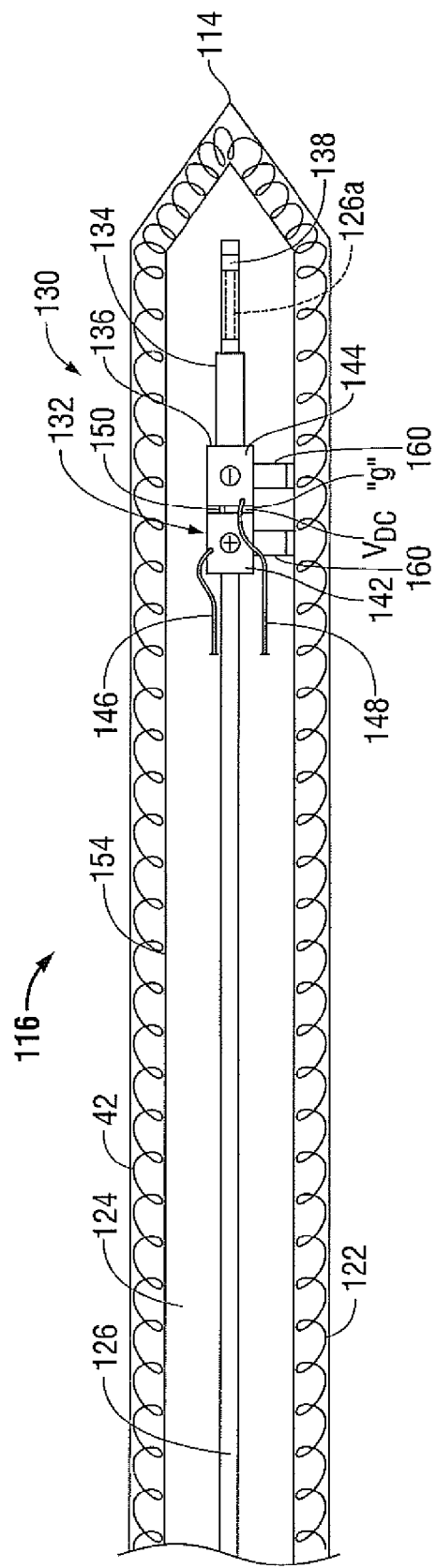
FIG. 6 is partial cut-away view of a distal tip of a microwave antenna according to an alternate embodiment of the present disclosure.

From the foregoing and with reference to the various figure drawings, those skilled in the art will appreciate that certain modifications can also be made to the present disclosure without departing from the scope of the same. For example, in an alternate embodiment, radiation detection device 130 (or operative components associated therewith) may be operably disposed internally along the shaft 112 adjacent radiating section 138 of microwave antenna 100 (FIG. 6) or internally along the feedline 520 adjacent radiating section 518 of microwave antenna 512. In the embodiment illustrated in FIG. 6, the resonator 130 including conductive members 142 and 144 and coaxial feed 134 are fixedly supported to catheter 154 via a pair of supports 160. Operation of the radiation detection device 130 and operative components associated therewith function in a manner as described above with respect to the radiation detection device 130 being disposed within the handle 118 and, as result thereof, will not be described in further detail.

It is contemplated that one or both of the conductive portions 142 and 144 may be coated with an insulative coating or sheathing (not shown) configured to insulate or electrically isolate the conductive portions 142 and 144 (or other operative components associated with the resonator 132) from one another and/or surrounding components associated with the microwave antenna 100. More particularly, proximal and distal edges of the respective conductive portions 144 and 142 may include an insulative material (not explicitly shown) to prevent shorting between the conductive members 142 and 144. Alternatively, or in combination therewith, an outer peripheral surface of one or both of the conductive portions 142 and 144 may be coated or formed from an insulative material.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system for monitoring ablation size, comprising:
   a power source including a microprocessor for executing at least one control algorithm;
   a microwave antenna configured to deliver microwave energy from the power source to tissue to form an ablation zone; and
   a radiation detection device operably disposed on the microwave antenna, the radiation detection device configured to generate a voltage corresponding to a radius of the ablation zone, wherein the radiation detection device is in operative communication with at least one module associated with the power source, wherein the at least one module triggers a signal when a predetermined threshold voltage is measured corresponding to the radius of the ablation zone,
   wherein the at least one module includes an ablation zone control module in operative communication with a memory associated with the power source, the memory including at least one data look-up table including rectified dc voltages associated with the microwave antenna, the rectified dc voltages corresponding to a radius of the ablation zone, the ablation control module configured to instruct the power source to adjust the amount of microwave energy being delivered to the microwave antenna when a signal from radiation detection device is received at the ablation zone control module to create a uniform ablation zone of suitable proportion with minimal damage to adjacent tissue.

2. A system according to claim 1, wherein at least a portion of the radiation detection device is operably positioned at a distal end of a handle associated with the microwave antenna and extends within an internal portion of a shaft associated with the microwave antenna.

3. A system according to claim 1, wherein the ablation zone control module and radiation detection device are activated when the power source is activated.

4. A system according to claim 1 wherein the ablation zone control module and radiation detection device are activated when the power source is deactivated.

5. A system according to claim 1, wherein the microwave antenna is configured to produce an ablation zone that is one of spherical and ellipsoidal.

6. A system according to claim 1, wherein the microwave antenna is configured to produce an ablation zone that is ellipsoidal.

7. A system according to claim 1, further comprising:
   at least one fluid pump configured to supply a cooling fluid to the microwave antenna for facilitating cooling of one of the microwave antenna and tissue adjacent the ablation zone.

8. A system according to claim 1, wherein the radiation detection device includes a resonator in electrical communication with a resonator coaxial feed extending distally along a length of a shaft of the microwave antenna, a distal end of the resonator coaxial feed positioned adjacent a radiating section of the microwave antenna and configured to detect radiation during the delivery of microwave energy from the power source to tissue and induce an electromagnetic field within the resonator such that a rectified dc voltage is generated at the resonator and communicated to the ablation zone control module.

9. A system according to claim 8, wherein the resonator made from a metal selected from the group consisting of copper, silver, gold, stainless steal, chrome and brass.

10. A system according to claim 8, wherein a dielectric coating is disposed between the shaft and the resonator coaxial feed to prevent electrical shorting between the resonator coaxial feed and the shaft.

11. A system according to claim 8, wherein the resonator coaxial feed is made from a metal selected from the group consisting of copper, silver, gold, stainless steal, chrome and brass.

12. A system according to claim 8, wherein the resonator is a substantially enclosed structure configured to resonate an electromagnetic field within the resonator.

13. A system according to claim 12, wherein the resonator is generally cylindrical.

14. A system according to claim 13, wherein the resonator includes a generally circumferential gap dividing the resonator into two conductive portions in electrical communication with one another and electrically isolated from one another, the two conductive portions in electrical communication with the ablation zone control module via a pair of conductive leads.

15. A system according to claim 14, wherein at least one diode extends across the generally circumferential gap and operably couples to each of the two conductive portions of the resonator, the at least one diode configured to produce a rectified dc voltage that corresponds to the electromagnetic field within the resonator.

* * * * *